United States Patent [19]

Mattchen

[11] 4,203,222
[45] May 20, 1980

[54] AUTOMATIC CHUCK FOR DRILL

[75] Inventor: Terry M. Mattchen, Van Nuys, Calif.

[73] Assignee: American Safety Equipment Corporation, Encino, Calif.

[21] Appl. No.: 3,657

[22] Filed: Jan. 15, 1979

Related U.S. Application Data

[63] Continuation of Ser. No. 712,729, Aug. 9, 1976, abandoned.

[51] Int. Cl.² .............................................. A61C 1/10
[52] U.S. Cl. ..................................... 433/129; 279/4; 279/75
[58] Field of Search ................. 32/26; 279/1 B, 4, 22, 279/30, 57, 74, 75; 408/5, 6; 415/503

[56] References Cited

U.S. PATENT DOCUMENTS

| | | |
|---|---|---|
| 3,692,321 | 9/1972 | Shattuck ................................... 279/4 |
| 3,698,729 | 10/1972 | Scherfen .................................. 279/4 |
| 3,712,386 | 1/1973 | Peters ...................................... 279/4 |
| 3,724,563 | 4/1973 | Wickham et al. ....................... 279/4 |
| 3,775,851 | 12/1973 | Flatland .................................. 32/26 |
| 4,033,039 | 7/1977 | Lohn et al. .............................. 32/26 |

FOREIGN PATENT DOCUMENTS

| | | |
|---|---|---|
| 688048 | 1/1930 | France .......................................... 32/26 |
| 834786 | 5/1960 | United Kingdom ........................ 32/26 |

*Primary Examiner*—Louis G. Mancene
*Assistant Examiner*—John J. Wilson
*Attorney, Agent, or Firm*—Poms, Smith, Lande & Rose

[57] ABSTRACT

A surgical tool has a pneumatically driven rotor motor, a source of air under pressure to drive the motor, an output system for receiving rotation from the motor and transmitting it to a bur and a securing system for securing the bur to the output system. The securing system receives air pressure from the source of air and converts the pressure to a force acting on the bur to grip the bur. The motor has a shaft mounted for rotation in a housing, and the shaft is hollow so that some of the air directed into the motor goes through the shaft and into a chamber. A piston is mounted in the housing, and when air from the shaft is directed into the chamber, it moves the piston in the chamber. The piston is connected to a collet, so that introduction of air into the chamber moves the collet. The collet has an inclined surface, and there are grippers between the inclined surface and the bur. As the collet moves so that the narrower portion of the inclined surface contacts the grippers, the grippers are urged against the bur to secure it. The piston is connected to the collet by a connection allowing relative movement therebetween so that when the piston moves to its release position while static friction from the grippers holds the collet means against the grippers, the piston can move toward a releasing position to provide a jerk on the collet to overcome static friction and move the collet to a releasing position.

20 Claims, 19 Drawing Figures

AUTOMATIC CHUCK FOR DRILL

This is a continuation of application Ser. No. 712,729, filed Aug. 9, 1976, now abandoned.

BACKGROUND OF THE INVENTION

This invention relates generally to surgical tools and to systems for holding the bur therein. Much surgery today uses power drills and other tools. Because the tools must be small and portable for use in the operating room, the large forces associated with power tools are developed over small areas creating many design problems. One such problem concerns mounting a bur on the surgical tool and securing it for rotation in view of the high torque that may be developed.

Some surgical drills use a threaded chuck. Rotating the chuck urges members against the bur. Although such an arrangement is simple, it creates problems. Hand tightening of the chuck is usually insufficient because of the high torque developed by the tool. The chuck must be of a relatively small diameter in order to not restrict viewing the work area or interfere with surrounding tissue, but smaller chucks make manual tightening ineffective. A wrench or other tool is usually required for tightening and loosening the chucks. Wrenches can be misplaced easily, and misplacing a wrench prevents use of the drill. Also, it is time consuming to use a wrench.

Automatic chucks have been proposed. For example Lieb, U.S. Pat. No. 3,631,597 (1972) teaches a collet locking arrangement which is driven forward by members moving in a helical slot. The linkage is somewhat complicated and adds to the bulk of the tool.

It is an object of the present invention to provide an automatic chuck for a surgical tool which is locked upon initiation of the rotary motor. A further object of the present invention is to use the air which drives the pneumatic rotor motor to lock the bur in the drill. Another object is to provide a gripping system for the tool which holds the bur securely in the tool and yet will not jam locked. Still another object of the invention is providing a mechanism to jerk the grippers holding the bur loose to overcome any static friction that may have built up in the tool. It should be recognized that although the discussion herein is primarily concerned with surgical tools, the automatic chuck is applicable to any tool using a rotating member such as a drill or bore. Other objects will become evident in the discussion of the invention, and it will be shown how they and the aforesaid objects are met.

SUMMARY OF THE INVENTION

With the foregoing objects in mind, the present invention includes a surgical tool having a pneumatically driven rotary motor, a source of air under pressure to drive the motor, output means for receiving rotation from the motor and transmitting it to a bur and securing means for securing the bur to the output means. This conventional system has been improved by having the securing means comprise transmission means for receiving air pressure from the source of air and converting the pressure to a force acting on the bur to grip the bur. The transmission means includes a chamber on the output member for receiving air and a piston in the chamber is driven out of the chamber when pressurized air flows into the chamber. Movement of the piston urges the securing means against the bur. The securing means includes a collet which has an inclined surface around the bur. Grippers in the form of wafers are mounted in a support around the bur for movement toward and away from the bur. When the piston moves the collet in one direction, the smaller diameter portion of the inclined surface of the collet forces the wafers against the bur. The source of air that directs air to the chamber to move the piston also directs air to the pneumatic rotor motor. The motor is mounted on a shaft in a housing, and the shaft is hollow to conduct air from the source of air. The shaft has a conduit which opens into the chamber.

The gripper and collet are designed so that the securing means will not lock in the securing position. Each wafer has a curved surface facing the inclined surface of the collet with a ball having a diameter smaller than the length of the wafer resting on the curved surface. When the collet moves forward under urging from the piston, it forces the ball against the wafer to urge the wafer against the bur. However, the ball rests at the forward end of the wafer and the curved surface directs force from the ball onto the collet in a direction angled to the axis of the bur and generally rearward on the tool. Therefore, once the piston is released, the force from the gripper is to move the collet to the releasing position. In order to overcome static friction in the securing means, the connection between the transmission means and the collet has some give to it so that the transmission means can move to the releasing position before movement of the collet begins. Once the transmission means and the collet grab each other, the additional momentum of the transmission means is sufficient to overcome static friction in the collet and jerk it to the releasing position.

DETAILED DESCRIPTION OF THE PREFERRED EMBODIMENT

1. Pneumatic Control

Referring first to FIGS. 3 and 12 through 15, the distribution of air is shown. The "air" that is used is normally nitrogen or other inert gas. However, the nitrogen is often referred to as "air", and that practice will be followed herein.

An air hose (not shown) is attachable to the right or rear end 11 of the tool housing 10 of the present invention. The hose used has an inner passage for carrying high pressure air from a source to the tool and an outer passage for conducting away exhaust air. Such hoses are conventional. The hose is connected to fitting 13 so that the inner conduit of the hose intersects with primary air conduit 14. The exhaust passage of the hose aligns with exhaust conduit 15 of fitting 13 so that the exhaust gases are transmitted into the hose for being exhausted away from the surgical tool.

Fitting 13 is mounted for swiveling on the rest of the tool so that the tool can be positioned irrespective of the orientation of the hose. Fitting 13 is attached to coupling 16 which is mounted for rotation on tool housing 10. Coupling 16 includes a central coupling conduit 17 which cooperates with primary air conduit 14 to direct air into inlet tube 18. By rotating coupling 16, the orientation of fitting 13 with respect to the rest of tool 10 is modified. Additionally, O-rings 19 and 20 are provided for sealing coupling 16 to housing 10 and fitting 13 to coupling 16.

Figure 3:
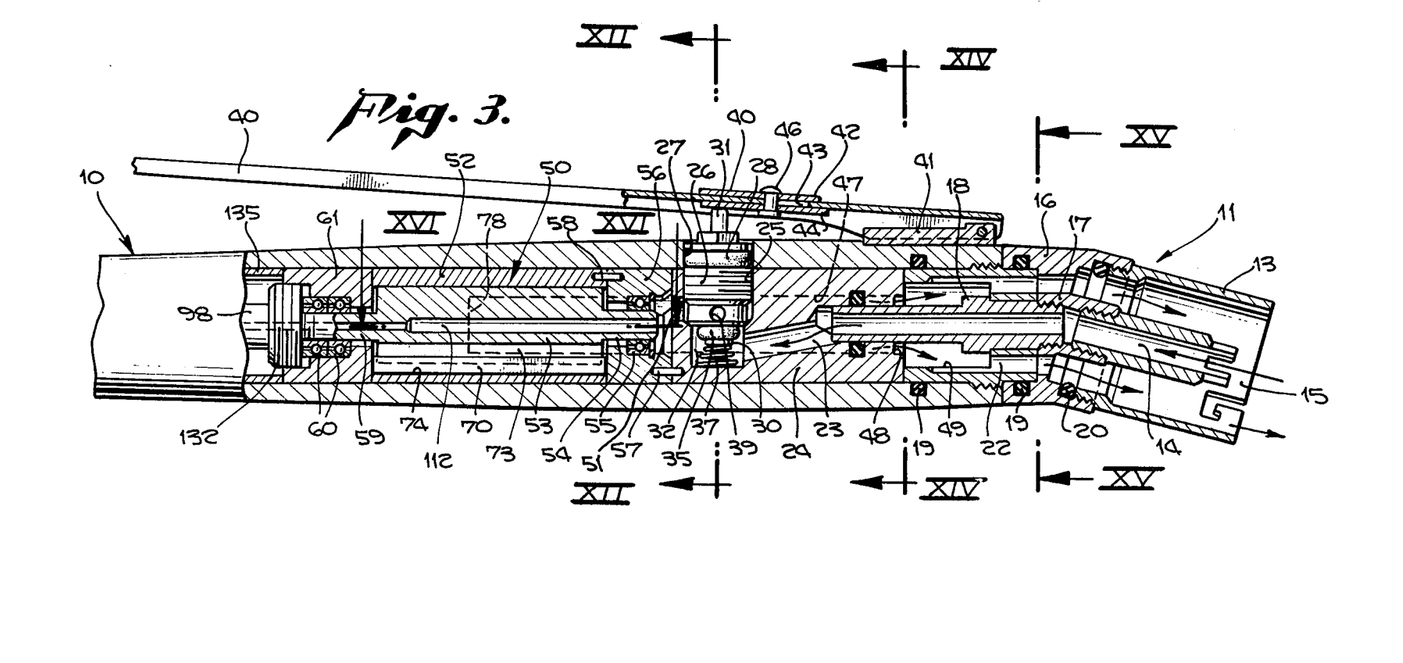
FIG. 3 is a side view in section showing the detail of the vane motor and the air distribution system.
Figures 12, 13:
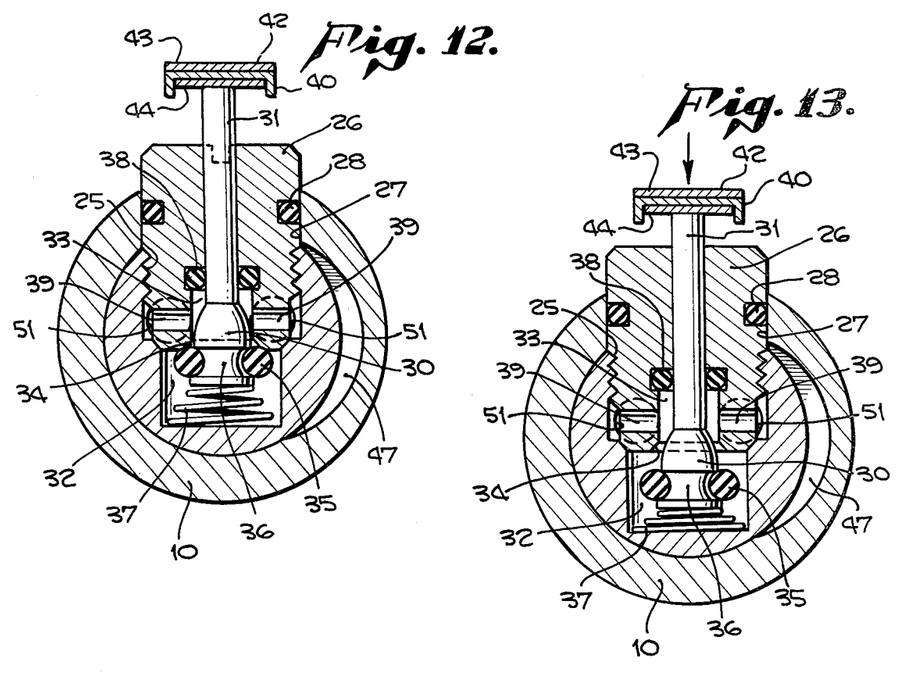
FIG. 12 is a sectional view taken through plane XII—XII in FIG. 3 showing the detail of the valve for the air motor of the present invention.
FIG. 13 is a sectional view similar to FIG. 12 showing the valve in the open configuration.

Inlet tube 18 is supported in stackup ring 21 that is supported in housing 10 of the tool. As more clearly shown in FIG. 15, stackup ring 21 has a plurality of spaced apertures 22 for conducting exhaust air in a manner set forth below. The air passes through inlet tube 18 and then to inlet channel 23 in valve body 24. Valve body 24 has an opening 25 for receiving poppet retainer 26 which is threaded into valve body 24 and sealed by O-ring 28. Opening 25 corresponds with another opening 27 through housing 10 so that part of the valve extends out of the housing. (FIGS. 3, 12 and 13).

The valve includes a poppet 30 mounted in poppet retainer 26. Valve stem 31 is attached at one end of poppet 30 and extends out of poppet retainer 26 and housing 10 to be depressed by the user. It is sealed by O-ring 38 which prevents air from leaking past the valve stem. The valve includes an inlet chamber 32 (FIGS. 12 and 13) that is connected to channel 23 so that high pressure air is directed into inlet chamber 32. Poppet 30 in the closed position seats on shoulder 34 of poppet retainer 26 to prevent air from flowing from inlet chamber 32 to outlet chamber 33. O-ring 35 in groove 36 helps create a seal between poppet 30 and seat 34, and spring 37 biases the poppet to the closed (FIG. 12) position. When valve stem 31 is depressed by depressing lever 40, poppet 30 moves to the FIG. 12 position to allow air to pass from inlet chamber 32 to outlet chamber 33.

Poppet 30 is preferably in the shape of an eccentric sphere. It has been found that that shape provides the greatest control for the air passing between chambers. When the valve is depressed slightly, less air will pass than if the poppet is in its fully opened position. The shape of the poppet provides maximum control of the amount of air.

After air reaches outlet chamber 33, it passes through openings which lead to the inlet conduit 51 of the rotor motor to drive the motor. The operation of the motor is explained in further detail below.

Figures 1, 2:
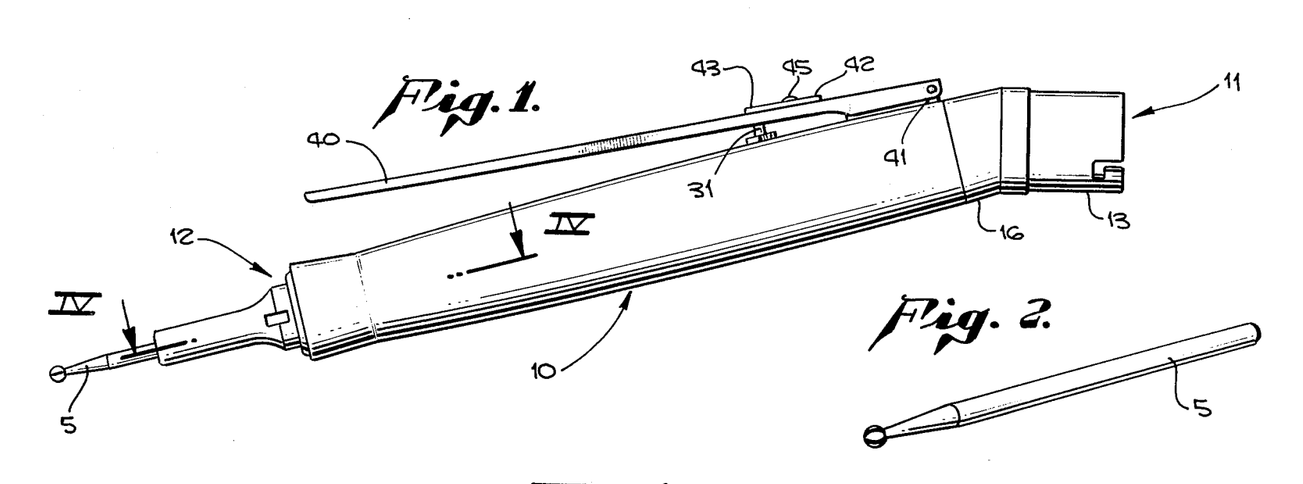
FIG. 1 is a side elevational view of the surgical tool of the present invention.
FIG. 2 is a perspective view of a bur that can be used with the surgical tool.

Lever 40 which is used to depress valve stem 31 is of conventional design. It is mounted for pivoting on support 41 (FIGS. 1 and 3) and extends toward front end 12 of the tool so that it is reachable by the surgeon. Moving lever 40 downward against housing 10 causes part of the handle to depress valve stem 31 moving poppet 30 off seat 34 to allow air to the motor.

A safety 42 is mounted for sliding on handle 40. The handle has an aperture (not shown) directly above the end of valve stem 31. Safety 42 is slidable over the opening and is presented to the end of valve stem 31. When safety 42 is not covering the opening, movement of handle 40 downward toward the housing 10 causes the valve stem 31 to go into the opening of the handle with no effect on the valve. When the safety is moved to a position covering the opening, similar movement of the handle causes safety 42 to drive valve stem 31 downward. Safety 42 is of somewhat conventional construction. It consists of two plates 43 and 44 riveted together by rivet 45 which can slide in slot 46 on handle 40. A modified safety is discussed in my copending application Ser. No. 712,728, filed Aug. 9, 1976.

Figure 14:
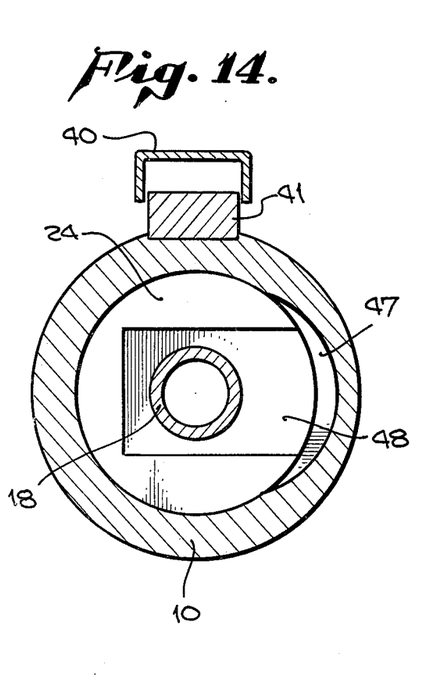
FIG. 14 is a sectional view taken through plane XIV—XIV in FIG. 3 showing some of the ports for passing pressurized and exhaust air in the tool.
Figure 15:
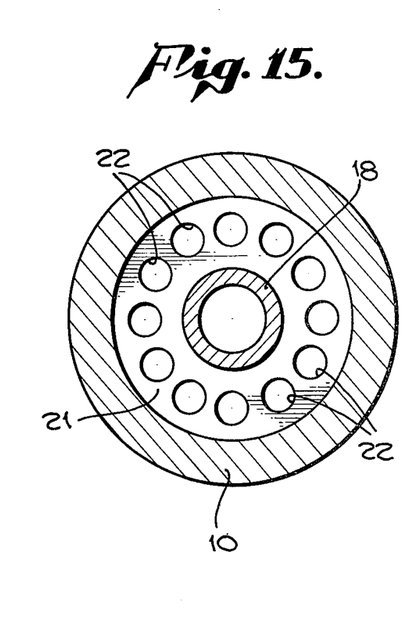
FIG. 15 is a sectional view taken through plane XV—XV in FIG. 3 showing other air passages in the present invention.
Figure 16:
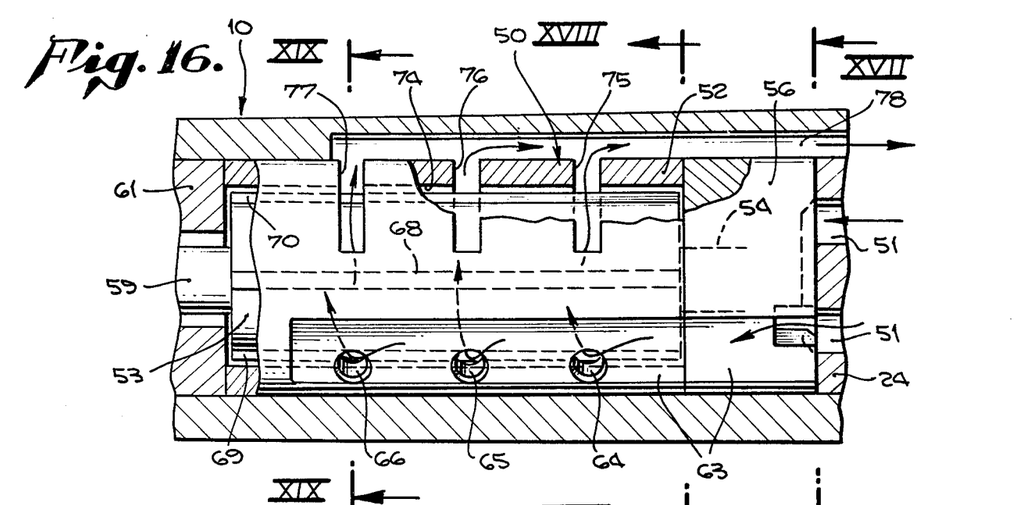
FIG. 16 is a sectional view of the rotor motor of the present invention and is taken through plane XVI—XVI in FIG. 3.
Figure 17:
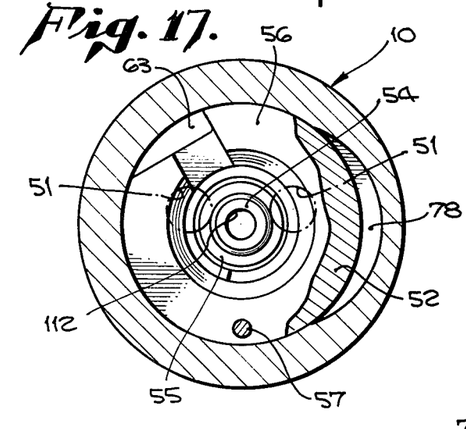
FIG. 17 is a sectional view taken through plane XVII—XVII in FIG. 16.
Figure 18:
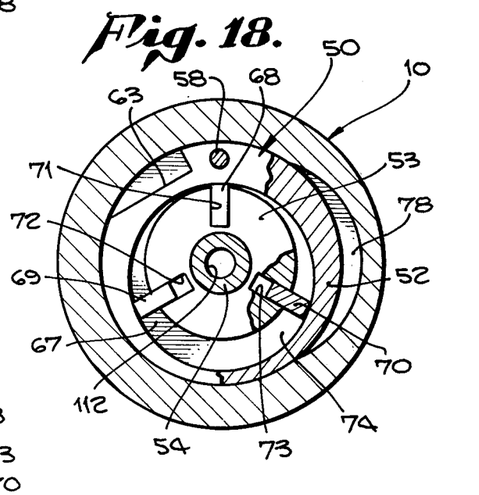
FIG. 18 is a sectional view taken through plane XVIII—XVIII in FIG. 16 showing a sectional view of the vanes of the rotor motor.

The exhaust system of the motor includes an exhaust chamber between valve body 24 and housing 10. The exhaust chamber 47 is best shown in FIGS. 12, 13 and 14. Exhaust chamber 47 opens into slot 48 (FIG. 14) on the end of valve body 24, through chamber 49 and into apertures 22 on stackup ring 21. After the exhaust air passes through apertures 22, it enters exhaust conduit 15 where it is conducted away from the tool.

There should be no restrictions in the exhaust system because it is important to maintain a low pressure therein. Restrictions that would raise the pressure create a back pressure on the motor and make it operate inefficiently.

2. The Motor

The motor of the present invention is a pneumatically driven vane motor used because it develops high torque even at low rpm. It is best seen in FIGS. 16 through 19 although its placement in the tool is also shown in FIG. 3. Motor 50 includes a motor housing 52 mounted in tool housing 10. Shaft 53 is mounted for rotation in motor housing 52, and the shaft extends rearwardly to a projection 54 supported on bearing race 55 in rear plate 56. Rear plate 56 is mounted in housing 10 and is pinned at 57 and 58 to valve body 24 and motor housing 52 respectively. Shaft 53 also has a forward projection 59 which is supported for rotation in bearings 60 mounted in forward plate 61.

Figure 19:
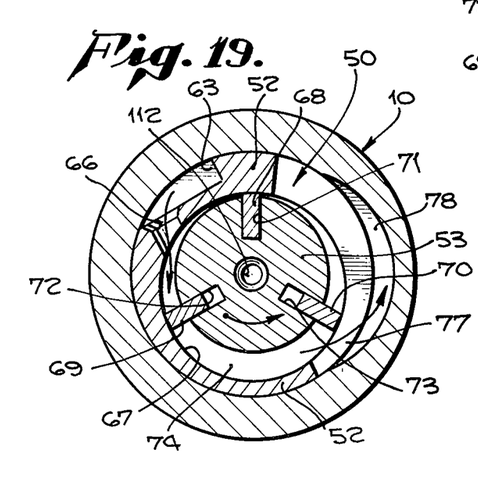
FIG. 19 is another sectional view taken through plane XIX—XIX of FIG. 16 also showing the operation of the vane motor.

Turning again to FIG. 16, pressurized air from the valve is directed through inlet conduit 51 to high pressure channel 63 and through inlet ports 64, 65 and 66. As shown in FIG. 19, the axis of rotation of shaft 53 is at the center of the housing 10. However, central bore 67 through motor housing 52 has an axis spaced from the axis of the shaft. This feature is noticeable in FIGS. 18 and 19 where the lower part of motor housing 52 is thinner than the upper portion.

Shaft 53 has a plurality of vanes 68, 69 and 70 mounted in slots 71, 72 and 73 in the shaft. Because shaft 53 is mounted eccentrically with respect to bore 67, expansion chamber 74 is of the shape shown in FIGS. 18 and 19.

As the high pressure air enters expansion chamber 74 through ports 64–66, it pushes against vane 69 and tends to expand to drive shaft 53 in a counterclockwise direction (FIG. 19). Eventually vane 69 reaches a position where the air can escape through exhaust slot 77. In the exemplary embodiment, there are three exhaust slots for transmitting the exhaust air to exhaust conduit 78 which in turn communicates with exhaust chamber 47, to exhaust the air out of the tool.

Because of the shape of expansion chamber 74, as shaft 53 rotates in the counterclockwise direction, the air on the inlet side of the vane is at a higher pressure than the air on the exhaust side at least until the vane reaches a position where the air can be exhausted through slots 75–77. The pressure differential causes rotation. The spring bias maintains the vanes against the inside walls of motor housing 52 so there is little leakage of air past the vanes. The exhaust area is much larger than the inlet area in order to lower back pressure which would make the motor run inefficiently.

This type of motor, although conventional, is very useful in this tool. High torque is developed, and the motor will not stall at low rpms as turbine motors may.

Rotational output from the shaft of the motor causes an output means to rotate. The output means transmits the rotation to bur 5 in a manner discussed below. Also discussed is the securing means for securing the bur to the output means.

It should be recognized that the air control system and the rotor motor operate on the same principles as the systems described in my copending application Ser. No. 712,730, filed Aug. 9, 1976. Attention is also drawn to my copending application Ser. No. 712,728, filed Aug. 9, 1976.

3. The Securing Means

Figure 4:
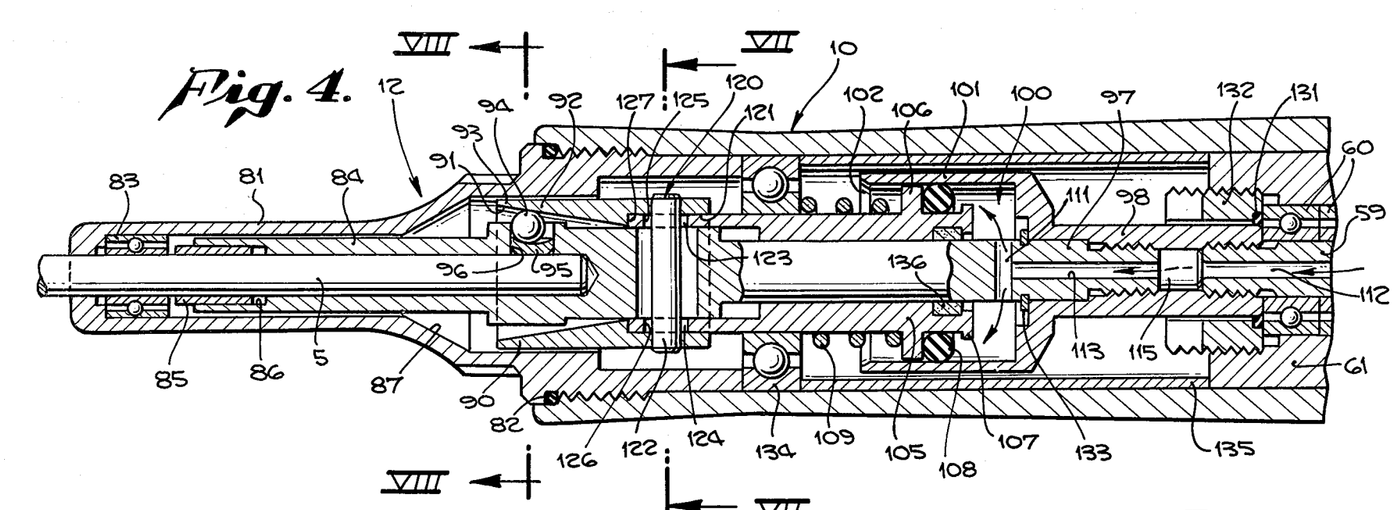
FIG. 4 is a sectional view taken through plane IV—IV of FIG. 1 showing details of the improved securing means of the present invention.
Figure 9:
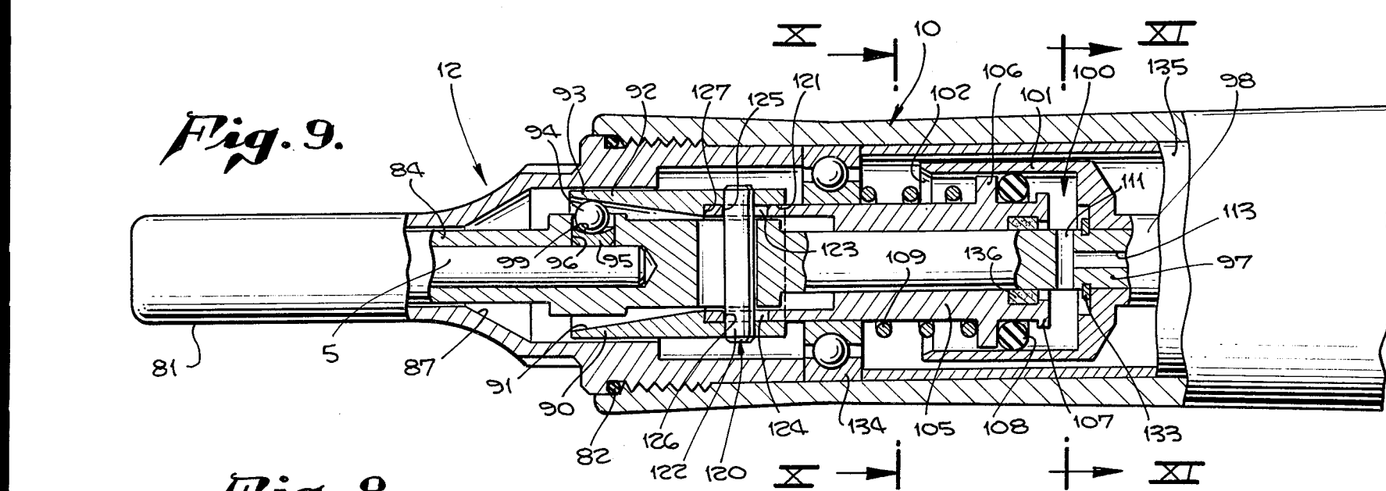
FIG. 9 is a sectional view similar to that shown in FIG. 4 but with the piston in the releasing position about to jerk the collet.
Figure 10:
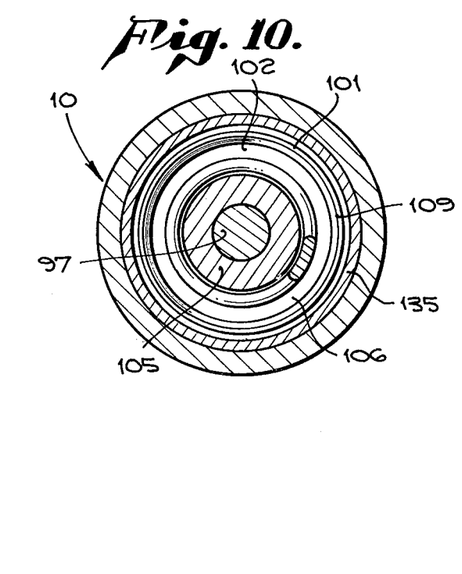
FIG. 10 is a sectional view taken through plane X—X in FIG. 9.
Figure 11:
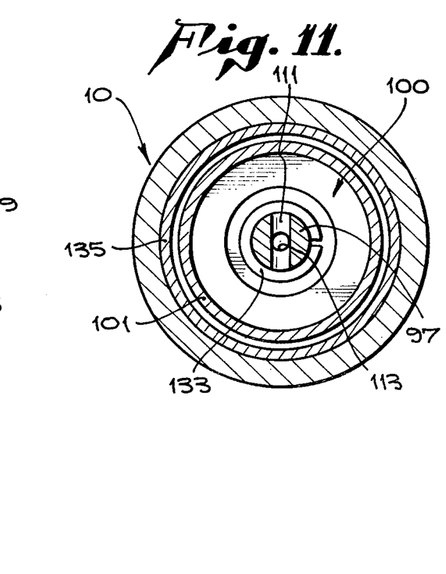
FIG. 11 is another sectional view taken through plane XI—XI in FIG. 9.

The automatic chuck or securing means of the present invention has a number of novel features. First discussed is the securing means itself. Turning to FIGS. 4 and 9, a nose piece 81 is threadably mounted in forward end 12 of the housing 10 with O-ring 82 acting as a seal therebetween. Although nose piece 81 is removable from housing 10, it is intended that removal would only take place for repairs. The primary purpose of nose piece 81 is to support bur 5 in order to prevent vibration when the bur is rotating. A bearing race 83 is mounted in nose piece 81 to decrease friction from the rotating bur. Supporting means 84 which is operably connected to the rotor motor and rotates therewith in a manner described hereinafter extends into nose piece 81 for further supporting the bur. Additionally, supporting means 84 is counterbored at 86 to receive bur supports 85 which rotate with supporting means 84 and help steady bur 5. Bur supports 85 also present a small frictional force to the bur to prevent it from falling out of the tool when it is inserted in supporting means 84.

The securing means also includes a collet means 90 which has an inclined surface 91 around bur 5. Inclined portion 91 has a narrower portion 92 and a wider portion 93. Gripping means are also provided between the inclined surface in the bur. In the exemplary embodiment, gripping means comprises balls 94 and wafers 95 which will be discussed in greater detail hereinafter.

Figure 5:
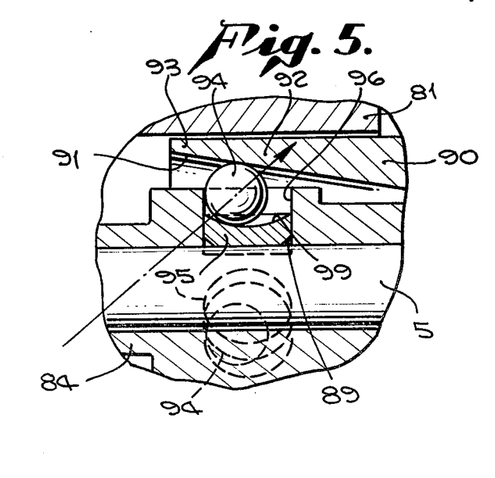
FIG. 5 is a sectional view showing in detail the collet contacting the ball which urges the wafer against the bur.
Figure 6:
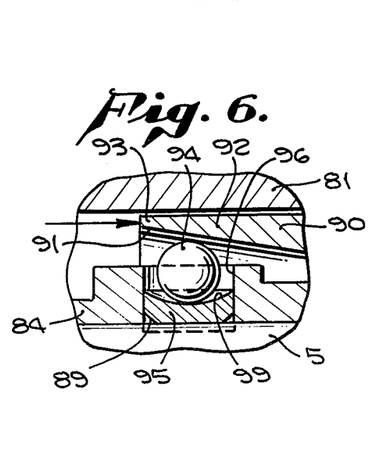
FIG. 6 is a view similar to FIG. 5 except that the collet is in the releasing orientation.

A transmission means, also discussed in detail below moves the collet means between a closing position (FIGS. 4 and 5) wherein the narrower portion 92 of the collet 90 contacts the gripping means (ball 94 and wafer 95) to urge the wafer against the bur to grip it. The transmission means also permits the collet to assume a releasing position wherein wider portion 93 of collet 90 is over the gripping means without urging the gripping means against the bur. (FIG. 6)

One of the improvements of the present invention is that the transmission means, which moves collet 90 between the securing and releasing positions, receives air pressure from the source of air and converts the pressure to a force acting on the bur to grip the bur. Essentially, the transmission means which includes chamber 100 and piston 105 receives air pressure to move piston 105 which in turn moves the collet. Referring to FIG. 4, output member 97 rotates with forward projection 59 of shaft 53 as both are connected to coupling member 98. The supporting member 84 is formed integrally from output member 97 so that rotation of motor shaft 53 and extension 59 rotates coupling 98, output 97 and supporting member 84.

The transmission means includes chamber means on the output means for receiving air pressure from the source of air and a piston in the chamber for being driven out of the chamber when pressurized air flows into the chamber, whereby movement of the piston urges the securing means against the bur. In the exemplary embodiment, chamber means 100 has an outer wall 101 which is integrally formed with coupling member 98. Piston 105 is mounted in chamber 100 around output member 98, and piston 105 extends out of the forward facing open end 102 of the chamber. Piston 105 includes an annular shoulder 106 extending to chamber wall 101. A smaller annular flange 107 extends outward from the rear (right in FIG. 4) end of piston 105, and an O-ring 108 is mounted between flange 107 and shoulder 106 and extends from the outside wall of piston 105 to the inside chamber wall 101. O-ring 108 and shoulder 106 cooperate to prevent air from leaking out of the chamber.

Air under pressure is directed to air port means 111 in a manner described hereinafter. From the air port means, the air can flow into the chamber where it creates a pressure in chamber 100 to create a force on all rear facing surfaces such as shoulder 106 and flange 107 of the piston.

The piston is biased to the right (FIG. 4) into chamber 100 by spring 109. Upon introduction of air into the chamber, piston 105 is urged to the left (FIG. 4). The piston is connected to the collet and it can drive the collet to the left so that the narrower portion 92 of inclined surface 91 contacts ball 94 urging wafer 95 against bur 5.

One of the important features of the present invention is the means for directing air into the chamber. Referring again to FIG. 3, motor shaft 53 has a central bore 112 therethrough. Bore 112 acts as a conduit conducting air from inlet conduit 51 to the chamber.

As shown in FIG. 4, air from shaft bore 112 passes into conduit 113 through output means 97 whereby air is conducted from a conduit in the shaft (bore 112) into conduit 113 in the output means. Air port means 111 on the output means in chamber 100 intersects conduit 113 for directing air from the conduit to chamber 110.

When the valve is opened and air is directed to vane motor 50, some of the air will pass through bore 112 where it passes into conduit 113 and then out of air port 111 to pressurize chamber 100. This action urges the securing means against bur 5 as discussed above. Therefore, the securing means is activated upon motor activation and occurs simultaneously therewith.

When motor 50 is stopped by closing the valve, the pressure in chamber 110 is dissipated through conduit 113 and bore 112 back to inlet conduit 51 where it can be dissipated through the vane motor. The decrease in pressure in chamber 110 allows spring 109 to urge piston 105 to the right (FIG. 4) which urges collet 90 to the right presenting the wider diameter portion 93 of inclined surface 91 over ball 94 to release wafer 95 from being urged against bur 5.

The dissipation of air pressure in the chamber occurs at different rates depending on the design of the tool and the speed of the tool prior to closing the valve. If air is released too quickly, wafers 95 may release bur 5 before rotation stops. This might permit a rapidly rotating bur to vibrate out of the supporting member 84 and create a somewhat dangerous condition. At high speed, bur supports 85 may not be able to prevent this. Therefore, the present invention contemplates a check valve for holding air in chamber 100 after air is no longer being directed to the motor for preventing release of bur 5 by the securing means while the motor is decelerating. In the exemplary embodiment, check valve 115, shown in schematic only in FIG. 4, is provided in the exemplary embodiment between bore 112 and conduit 113 to slow the flow of air from conduit 113 to bore 112 so that pressure is maintained in chamber 100 while bur 5 is decelerating.

Figure 8:
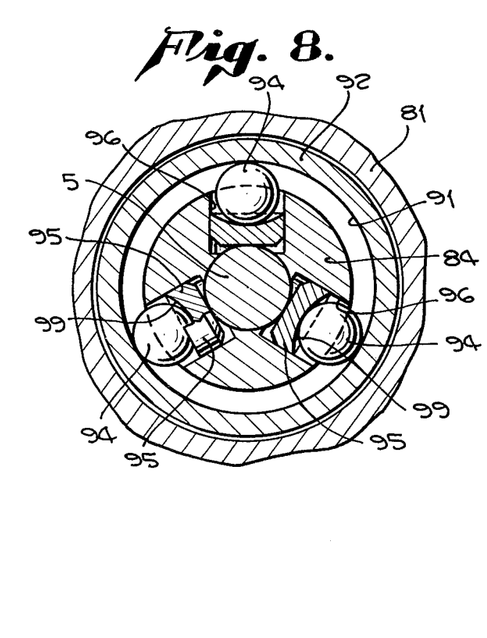
FIG. 8 is a sectional view taken through plane VIII—VIII in FIG. 4 showing the collet urging the balls against the wafers to grip the bur.

These gripping means of the present invention includes some important features. For example, wafers are mounted in supported means 84 for radial movement toward and away from the bur. In the exemplary embodiment, especially as shown in FIG. 8, three wafers 95 are equally spaced around supporting means 84 in openings 96 therethrough. The wafers are used to spread forces from ball 94 onto wafer 95 along a length of the bur.

Each wafer is a disc with surface 99 being a hemispherical depression in the disc. In the exemplary embodiment (FIGS. 5, 6 and 8), the depression extends to the outside edge of the disc but it could be somewhat smaller. However, the diameter of the depression is greater than the diameter of ball 94 which is received in the depression. This geometry transmits at least a portion of the forces from bur 5, wafer 95 and ball 94 on collet 90 at an angle (as opposed to perpendicular) to the longitudinal axis of the supporting means 84. Because the collet opens toward the front 12 of the tool, the angled force urges the collet to the releasing position. (See the arrow in FIG. 5.)

Wafer 95 could also be rectangular. Surface 99 would curve along the length of the wafer and have a length greater than the diameter of ball 94. The bottom surface could also be curved to conform to the bur's surface.

The angle can be modified by changing the curvature of surface 99 or the angle of inclined surface 91. If surface 99 is flat or incline 91 too shallow, the line of force may become vertical with large forces developing between ball 94, wafer 95, collet 90 and bur 5. This may jam the securing means in the securing position. If that happens, even though air pressure is released from the piston, the force from spring 109 may be insufficient to overcome the frictional forces created by jamming of the parts. Curved surface 99 assists in directing forces on the collet rearwardly to help overcome friction that may be created between the parts.

Each wafer is keyed into one opening 96 to prevent the wafer from falling into the center of supporting means 84 when no bur is present. Additionally, each wafer has a forward inclined edge 89 which is contacted by bur 5 when the bur is inserted into supporting means 84 to urge wafers 95 upward to allow insertion of bur 5.

If bur 5 is not completely inserted into supporting means 84 so that part of it is not under wafer 95, when supporting means 84 begins to rotate, vibrations from an unsecured bur could damage the tool or the bur or even potentially injure the patient. Therefore, means are provided on the tool for intersecting the collet when the collet travels beyond a normal securing position when no bur is in the securing means for stopping rotation of the collet and the output means whereby the output means is prevented from rotating a bur that is not secured by the securing means. In the exemplary embodiment, the means for intersecting collet means includes the sloping surface 87 of nose piece 81. The collet 90 is dimensioned such that if it is driven forward by piston 105 and there is no bur under wafer 95, the front end of collet 90 will intersect surface 87 of nose piece 81. Because the collet is rotated with rotation of output means 97, intersection of sloping surface 87 by collet 90 will prevent rotation of output means 97 and consequently supporting means 84 and bur 5.

Even though the present invention is designed to have ball 94 urge collet 90 to the releasing position as explained above with particular reference to FIG. 5, some static friction develops between the parts. It may be difficult for spring 109 to overcome this static friction, and providing a spring of increased strength slows the movement of piston 105 when it is desired to be activated. Therefore, a system has been developed to insure that static friction between wafer 95, ball 94 and collet 90 is overcome to release the bur.

The present invention has been improved by having connecting means connect the transmission to the collet and having means for allowing relative movement therebetween so that the transmission means can move toward its releasing position while static friction still holds the collet to the gripping means in the securing position. The connecting means also has means for securing the transmission means to the collet after the transmission means has moved toward its releasing position to provide a jerk from the moving transmission means on the collet to overcome the static friction and allow the collet to move to the releasing position.

Figure 7:
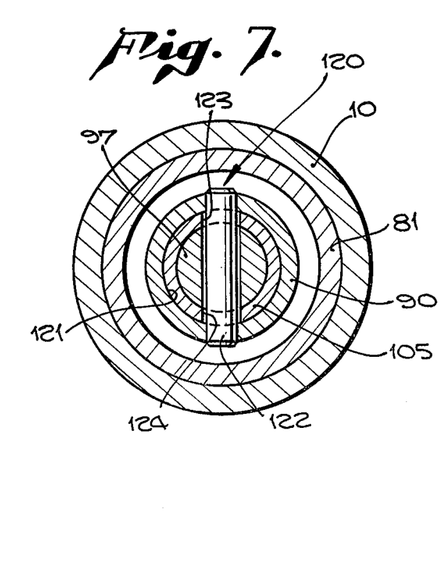
FIG. 7 is a sectional view taken through plane VII—VII in FIG. 4 and shows the connecting means which are provided for jerking the collet toward the releasing position to overcome static friction.

In the exemplary embodiment, especially FIGS. 4, 7 and 9, the connecting means 120 includes a bore 121 extending into the rear end of collet 90. Shaft 122 extends through bore 121 generally perpendicular to the axis of the bore. The transmission means, in this case piston 105, extends into bore 121 and has aperture means (apertures 123 and 124) for receiving shaft 122. The apertures have length dimensions parallel to the axis of the bore greater than the corresponding dimension of shaft 122 so that apertures 123, 124 can move longitudinally with respect to shaft 122 allowing relative longitudinal movement between the collet and the transmission means.

When air is no longer supplied to the transmission means (chamber 100 and piston 105), the piston begins to move to the right (FIG. 4) but the connecting means allows relative movement between piston 105 and collet 90. However, when front walls 125, 126 of apertures 123, 124 contact the shaft 122, the moving piston provides a jerk to collet 90. See FIG. 9. The movement of piston 105 in a sense converts the static friction between the gripping means and the collet into dynamic friction that is of a lower magnitude than the static friction so that the forces holding the parts together are less. The jerk or lowering of the forces is enough to overcome the friction and allow the collet to move with the piston to their releasing positions. When piston 105 is to be moved to the securing position, the front of the piston contacts front wall 127 of bore 121 to urge collet 90 forward (to the left in FIG. 4).

Rotation of the parts occurs as follows. As shaft 53 of motor 50 rotates, front projection 59 rotates in bearing race 55. Seal 131 prevents leakage and holds bearing 60 in place. The seal is held by threaded ring 132 (FIG. 4). Rotation of projection 59 rotates coupling 98 which in turn rotates chamber 100. Rotation of coupling 98 also rotates output member 97 which is threaded in coupling 98 and secured by locking spring 133. Piston 105 also rotates with the remaining parts because of its connection with shaft 122 which is rotated by output member 97. Although there is play for allowing longitudinal movement between piston 105 and shaft 122, rotation of the collet means relative to the piston is prevented because the sidewalls of apertures 123 and 124 contact the surface of the shaft. Because the shaft is rigidly held in collet 90, the positive rotation of the shaft by piston 105 positively rotates the collet. The rotation of the piston is supported by bearing 134 which is secured between the rear end of nose piece 81 and cylinder 135. A seal 135 may be provided about the end of piston 105.

The method contemplated by the present invention for securing bur 5 in the surgical tool that has an air motor 50 includes the steps of mounting bur 5 in securing means 84, moving collet 90 from a position releasing gripping means 94, 95 from the bur to a position securing the gripping means against the bur to grip the bur. The method has been improved by moving the collet between the releasing and securing positions with air pressure from air motor 50.

4. The Operation Of The Tool

When a new bur is to be used, it is inserted into nose piece 81 in securing means 84 as far in as possible. When lever 40 is depressed, the valve opens and air from the source can travel to vane motor 50. After rotating the motor, the air is exhausted out of the tool through exhaust conduit 15. Some of the air directed to the motor to drive it passes through bore 112 in shaft 53 of the motor where it is directed through conduit 113 and output means 98 to air ports 111 and into chamber 100. The buildup in air pressure urges piston 105 to the left in FIG. 4 out of the chamber which likewise urges collet 90 to the left creating a force on ball 94 to urge wafer 95 against bur 5. When lever 40 is released and the flow of air to the motor stopped, air in chamber 100 is dissipated back through conduit 113 and bore 112. The flow of air is slowed by check valve 115. The lower air pressure in chamber 100 allows piston 105 to move to the right under urging from spring 109. After it moves a small distance, it contacts shaft 122 which is connected to collet 90 to yank collet 90 off ball 94. This releases wafer 95 from bur 5 so that the bur may be removed from the tool.

The foregoing description has met all of the objects set forth above and shown certain evident objects. The invention has been explained with reference to the preferred exemplary embodiment, and it is understood that numerous modifications could be made in the embodiments while still within the scope of the invention and the appended claims.

I claim:

1. In a surgical tool having a pneumatically driven motor in a motor housing, a source of air under pressure to drive the motor, output means for being rotated by the motor and transmitting it to a rotating implement and securing means for securing the implement to the output means, the improvement comprising the provision of:

the securing means comprising transmission means for receiving air under pressure from the source of air and for converting the pressure to a force acting on the implement to grip the implement and passage means through the motor housing for directing air from the source of air to the transmission means.

2. The improvement of claim 1 wherein the motor comprises a motor shaft rotating in the motor housing in response to air pressure from the source of pressurized air acting on the motor, a conduit through the motor shaft connected at one end to the source of pressurized air and at the other end to the transmission means.

3. The improvement of claim 2, wherein the motor comprises vanes mounted on the motor shaft and contacting the motor housing, means for directing a portion of the air from the source of pressurized air between adjacent vanes and between the motor shaft and the motor housing for rotating the motor shaft and for directing a portion through the conduit through the motor shaft whereby when air rotates the rotor motor, it simultaneously activates the securing means.

4. The improvement of claim 1, wherein the transmission means comprises a chamber on the output means for receiving air from the source of air and a piston in the chamber for being driven out of the chamber when pressurized air flows into the chamber, whereby movement of the piston urges the securing means against the rotating implement.

5. In a surgical tool having a pneumatically driven rotary motor, a source of air under pressure to drive the motor, output means for receiving rotation from the motor and transmitting it to a bur, and securing means for securing the bur to the output means, the securing means comprising transmission means for receiving air pressure from the source of air and for converting the pressure to a force acting on the bur to grip the bur, the improvement comprising:

the transmission means comprising chamber means on the output means for receiving the air and piston means for being driven out of the chamber means when pressurized air flows into the chamber, whereby movement of the piston urges the securing means against the bur, and wherein the rotary motor comprises a motor housing, shaft means mounted for rotation in the motor housing, means to direct air into the motor housing and vane means for receiving the air and imparting rotation to the shaft means, exhaust means for exhausting air out of the motor housing after the air has driven the vane means, and conduit means through the shaft means for conducting air from the source of air through the motor housing into the chamber.

6. The improvement of claim 5 wherein the output means has a conduit therethrough intersecting the conduit in the shaft means whereby air is conducted from the conduit in the shaft means into the conduit in the output means, air port means on the output means in the chamber intersecting the conduit in the output means for directing air from the conduit in the output means to the chamber whereby when air is directed into the motor to activate the motor, air is directed into the chamber to urge the securing means against the bur.

7. The improvement of claim 6 further comprising check valve means for holding air in the chamber after air is no longer being directed into the motor for preventing release of the bur by the securing means while the bur is decelerating.

8. In a surgical tool having a pneumatically driven rotary motor, a source of air under pressure to drive the motor, output means for receiving rotation from the motor and transmitting it to a bur and securing means for securing the bur to the output means, the improvement comprising the provision of:

the securing means comprising transmission means for receiving air pressure from the source of air and for converting the pressure to a force acting on the bur to grip the bur, wherein the securing means comprises collet means movable between a securing position where it urges gripping means against the bur and a release position where the collet means releases the gripping means from the bur, the transmission means moving the collet means between the releasing and the securing positions, and connecting means between the transmission means and the collet for allowing relative movement between the transmission means and the collet means in the longitudinal direction whereby when the collet means is in the securing position and friction is developed between the collet means and the gripping means, when the flow of air is stopped, the transmission means can begin moving before it engages the collet means which provides a jerk from the transmission means to the collet means that overcomes the friction between the collet means and the gripping means.

9. In a surgical tool having a pneumatically driven rotary motor, a source of air under pressure to drive the motor, output means for receiving rotation from the motor and transmitting it to a bur and securing means for securing the bur to the output means, the improvement comprising the provision of:

the securing means comprising transmission means for receiving air pressure from the source of air and for converting the pressure to a force acting on the bur to grip the bur, wherein the securing means comprises collet means rotating with the output means movable between a securing position where it urges gripping means against the bur and a release position where the collet means releases the gripping means from the bur, the transmission means moving the collet means between the releasing and securing positions, and means on the tool for intersecting the collet means when the collet means travels beyond a normal securing position when no bur is in the securing means for stopping rotation of the output means whereby the output means is prevented from rotating a bur that is not secured by the securing means.

10. In a rotary tool having an automatic chuck for securing a bur in the tool, the automatic chuck having collet means movable between a securing position whereby the collet means urges gripping means against the bur and a releasing position releasing the gripping means from the bur, transmission means, and connecting means for connecting the transmission means to the collet means, output means interconnecting the motor with the transmission means for rotating the transmission means with the motor rotation, the connecting means connecting the transmission member to the collet means whereby rotation of the transmission member rotates the collet means to rotate the bur when the collet means is in the securing position, a spring attached to the transmission member for urging the transmission member to the releasing position, means associated with the transmission member for receiving pressurized air from the source of air and converting the air pressure force to a force urging the transmission member towards the securing position, the improvement comprising:

the connecting means further having means for allowing relative axial movement between the collet means and the transmission means, so that when the transmission means and collet means are in the securing position, the spring acts only on the transmission means to move the transmission means toward its releasing position while static friction from the gripping means holds the collet means in the securing position, the connecting means having means for axially securing the transmission means to the collet means after the transmission means has moved toward its releasing position whereby the inertia forces from the moving transmission means and the spring forces combine to overcome the static friction from the gripping means on the collet means to move the collet means to the releasing position.

11. The improvement of claim 10 wherein the connecting means comprises a bore extending into the collet means, a shaft extending through the bore generally perpendicular to the axis of the bore, the transmission means extending into the bore and having aperture means for receiving the shaft, the aperture means having a length dimension parallel to the axis of the bore being greater than the corresponding dimension of the shaft whereby the aperture can move longitudinally with respect to the shaft allowing relative longitudinal movement between the collet means and the transmission means.

12. The improvement of claim 11 comprising means for preventing rotation of the collet means relative to the transmission means.

13. The improvement of claim 11 wherein other side walls of the aperture contact other surfaces of the shaft for insuring positive rotation of the collet means by the transmission means.

14. The improvement of claim 10 comprising means for preventing rotation of the collet means relative to the transmission means.

15. In an automatic chuck for securing a bur to a rotary tool having support means for supporting the bur in the tool, output shaft means connected to an air driven motor and to the supporting means for transmitting rotation from the air driven motor to the supporting means, gripping means extending through the supporting means for gripping the bur, collet means having an inclined surface contacting the gripping means, the collet means being movable between a securing position wherein a narrower diameter portion of the inclined surface contacts the gripping means to urge it against the bur to grip the bur, the collet being movable to a releasing position having a wider diameter portion of the inclined surface contacting the gripping means without urging the gripping means against the bur, and collet moving means for moving the collet between the securing and the releasing positions, the improvement comprising the provision of:

the collet moving means comprising piston means connected to the collet means and means to direct air through the air driven motor to the piston means for moving the piston means to move the collet means from the releasing position to the securing position.

16. The improvement of claim 15 comprising chamber means attached to the shaft for rotation therewith, and for receiving air therein, air supply means for supplying air to the chamber under pressure, the piston means being received within the chamber for movement in a direction out of the chamber when air under pressure is introduced therein.

17. The improvement of claim 16 wherein the chamber means surrounds at least a portion of the output shaft means, the output shaft means having an axial air conduit therethrough and having port means connected to the air conduit opening into chamber means for directing air into the chamber.

18. The improvement of claim 17 wherein the air driven motor means has a motor shaft rotating in a motor housing in response to air pressure on the air driven motor means acting from a source of pressurized air, the motor shaft connected at one end to the source of pressurized air and at the other end to the output shaft means whereby air from the same source of air that operates the air driven motor means passes through the conduit to pressurize piston means to move the collet means to the securing position when the air driven motor is operating.

19. In a surgical tool having a pneumatically driven rotary motor, a source of air under pressure to drive the motor, output means rotating in response to the rotation of the motor and rotating an implement, and securing means for securing the implement to the output means, the improvement comprising the provision of:

securing means comprising collet means rotating with the output means movable between a securing position where it urges gripping means against the implement and a release position where the collet means releases the gripping means from the implement, the transmission means moving the collet means between the releasing and securing positions, and means on the tool for intersecting the collet means when the collet means travels beyond a normal securing position when no implement is in the securing means for stopping rotation of the output means whereby the output means is prevented from rotating an implement that is not secured by the securing means.

20. A method of automatically securing a bur in a rotating tool, the tool having a rotating motor in a motor housing powered by pressurized air from a source of air under pressure, the tool having securing means including a collet and pneumatic transmission means for closing the securing means to secure the bur to the tool upon application of pressurized air to the pneumatic transmission means, the method comprising:

directing the air under pressure to the rotating motor, directing a portion of the air through the motor housing to the pneumatic transmission means to close the securing means when the rotating motor is operating.

* * * * *